United States Patent [19]

Mendes et al.

[11] Patent Number: 5,698,562

[45] Date of Patent: Dec. 16, 1997

[54] PALATABLE TRIMETHOPRIM ORAL SOLUTION

[75] Inventors: Robert W. Mendes, Dedham; Nitin Pathak, Boston; Emmett Clemente, Manchester, all of Mass.

[73] Assignee: Ascent Pediatrics, Inc., Wilmington, Mass.

[21] Appl. No.: 772,926

[22] Filed: Oct. 8, 1991

[51] Int. Cl.$^6$ ................................................. A61K 31/505
[52] U.S. Cl. ........................................................... 514/275
[58] Field of Search .................................................. 514/275

[56] References Cited

U.S. PATENT DOCUMENTS

| | | | |
|---|---|---|---|
| 2,909,522 | 10/1959 | Hitchings | 544/325 |
| 3,985,876 | 10/1976 | Hazlett et al. | 514/275 |
| 4,198,429 | 4/1980 | Bartmann et al. | 424/52 |
| 4,645,662 | 2/1987 | Nakashima et al. | 560/121 |
| 4,935,225 | 6/1990 | Curtis et al. | 424/49 |
| 4,971,785 | 11/1990 | Wilson et al. | 424/44 |
| 5,338,732 | 8/1994 | Atzinger et al. | 514/178 |

OTHER PUBLICATIONS

"Trimethoprim in Pediatric Urinary Tract Infection" Child Nephrol. Urol. 1988–1989; 9: 77–81 Rajkumar et al.

Manius in: Flory, ed. *Analytical Profiles of Drug Substances*, vol. 7 (Academic Press, 1978), pp. 445–475.

*Primary Examiner*—Jeffrey C. Mullis
*Attorney, Agent, or Firm*—Hale and Dorr LLP

[57] ABSTRACT

This invention is directed to an aqueous pharmaceutical composition with 1.25 mg to about 10 mg trimethoprim per mL (wt/vol) of solution and a compound of suitable acid strength to permit the dissolving of trimethoprim at the appropriate concentration, with the composition having a pH of less than 6.0. This composition is particularly useful for pediatric oral use.

3 Claims, No Drawings

PALATABLE TRIMETHOPRIM ORAL SOLUTION

FIELD OF THE INVENTION

This invention is directed to a palatable oral solution of trimethoprim in a suitable concentration for pediatric dosing.

BACKGROUND OF THE INVENTION

Trimethoprim, U. S. P. (TMP) is a synthetic antibacterial agent which acts by selectively interfering with the biosynthesis of nucleic acids and proteins in bacteria. "The Pharmacological Basis of Therapeutics", 8th Edition, A G Gilman, T W Rall, A S Nies, P Taylor, eds., Pergamon Press. It is rapidly absorbed following oral administration and has a half-life of 8–10 hours. It is a white to light yellow, odorless, bitter compound with very poor solubility in water and alcohol. "Analytical Profiles of Drug Substances", Vol. 7, K Florey, ed., Academic Press.

Generally administered in combination with sulfamethoxazole, the most common dosage forms are tablet, oral suspension and intravenous solution. The adult dose of TMP alone is 100 mg twice daily; TMP-S is generally available as 80 mg TMP plus 200 mg sulfa per dose. There is currently no oral liquid TMP-only product available on the market, although there are TMP-only tablet products. "Physician's Desk Reference", 45th Edition, Medical Economics Company. Given the facts that (1) fixed combination drugs are generally less desirable than individual drug dosing, (2) that the microbial activity spectrum of the two drugs is essentially equivalent, and (3) recent studies indicate that TMP alone is as therapeutically effective as the combination therapy, it appears advantageous to develop such a product, especially for pediatric use. "Trimethoprim in Pediatric Urinary Tract Infections", *Child Nephrology and Urology*, 89 (9), 77–81 (1988).

From the perspectives of ease of use, accuracy of dose, and bioavailability, oral liquid dosage forms are generally preferred to be in the form of a solution. The general disadvantage of the oral solution is the tendency toward accentuating disagreeable taste contributed by the drug itself.

From the perspective of taste, oral liquid dosage forms are generally preferred to be in the form of a suspension which tends to mask the taste of the drug. The general disadvantages of the oral suspension are reduced accuracy and precision in dosing and reduced or delayed bioavailability.

Especially for pediatric use, where doses are relatively small, accuracy and precision of dose is extremely important. For this reason, the preferable oral liquid form for TMP is the solution rather than the suspension.

SUMMARY OF THE INVENTION

The desire for an oral solution dosage form of TMP is complicated by the fact that it is a bitter compound with poor solubility in water. It is not possible to form a solution of TMP in water at a sufficiently high concentration so as to provide the proper dose. Further, the bitterness of the drug must be masked to provide appropriate palatability.

The problem of solubility in water has been addressed in the case of the injection dosage form by the use of a high concentration of propylene glycol and alcohol as co-solvents, the drug being sufficiently soluble in the combination. However, such combination is extremely bitter and unpleasant tasting, making it completely unacceptable for oral use. The presence of propylene glycol, in fact, enhances the bitterness of the drug. Further, the use of alcohol is undesirable in pediatric formulations.

It was, therefore, an objective of the invention to discover a method of solubilization of TMP in water which would permit dissolving a sufficient concentration of the drug while, at the same time, providing a basis for appropriate sweetening and flavoring in order to make the combination acceptably palatable.

These and other objectives are achieved by the present invention which is directed to a pharmaceutical composition consisting of a palatable oral solution which contains trimethoprim in a suitable concentration for pediatric dosing. More specifically, the aqueous pharmaceutical composition is a combination of a sweetener, a flavoring, physiologically acceptable antimicrobial preservatives, and a vehicle of suitable acid strength to permit the dissolving of trimethoprim at the appropriate concentration. The trimethoprim is present in the aqueous pharmaceutical composition at a concentration of at least 1.25 mg to about 10 mg, and preferably 5 mg, per mL relative to the volume of solution. The composition further has a pH of less than 6.0.

DETAILED DESCRIPTION OF THE INVENTION

The composition of this invention is designed to be a palatable solution which is capable of delivering a therapeutic dose of trimethoprim in a form which is readily and rapidly absorbed from the gastrointestinal tract.

The sweetener of the composition may be any natural or synthetic compound, or combination of compounds, which provides adequate sweetening to overcome the bitterness of the drug. Natural sweeteners include carbohydrates such as sucrose, dextrose, fructose, invert sugar, mannitol, sorbitol, and the like. Synthetic sweeteners include saccharin, aspartame, cyclamates, and other so-called artificial sweeteners familiar to those of skill in the art. However, the inventors early research utilizing cosolvents such as alcohol, polyethylene glycols (PEG), propylene glycol, glycerin, and the like, proved fruitless in that the taste imparted by these solvents was additive to the already bad taste of the trimethoprim.

The flavoring of the composition may be any natural or synthetic compound, or combination of compounds, which provides acceptable taste to overcome the blandness of the base composition. Such flavorings include bubble gum, grape, cherry, berry, citrus, other fruits, peppermint, spearmint, other mints, vanilla, chocolate, and the like, familiar to those of skill in the art.

The antimicrobial preservatives of the composition include the derivatives of parahydroxybenzoic acid such as methyl paraben, propyl paraben, butyl paraben, and the like, benzoic acid and its derivatives such as sodium benzoate, benzyl alcohol, and other compounds approved for use as preservatives in orally administered drug products.

The vehicle of the composition includes water of suitable purity for use in orally administered drug products, and a strong, salt-forming acid of suitable strength to impart solubility of the trimethoprim and to adjust the hydrogen ion concentration of the composition to a pH of less than 6.0, typically using acid, such as hydrochloric acid or sulfuric acid. The preferred pH is in the range of 4.0 to 6.0.

The concept of using a strong acid to improve the solubility of TMP in order to achieve sufficient concentration without the use of non-aqueous cosolvents is critical to the formulation, since this permits appropriate sweetening and flavoring to allow for oral use. R Dahlin, C McDonald and V B Sunderland, "Solubilities and intrinsic dissolution rates of sulphamethoxazole and trimethoprim", *Journal of Pharmacy and Pharmacology*, 39, 246–251 (1987) discusses dissolution testing of TMP-sulfa tablets. The data showed that the solubility of TMP is markedly higher between pH 1.5 and 5.5, decreasing quickly above and below this range. It was shown that solubility remained poor at all pH's between 2 and 10 when adjusted with buffers of tartrate, acetate, phosphate and borate. The inventors interpreted this to indicate that pH adjustment alone was not sufficient to bring about dissolution, but that a strong salt-forming acid (such as hydrochloric acid or sulfuric acid) is necessary. On this basis, the inventors studied the effect of using strong acid to solubilize the TMP and permit the formulation of a taste-acceptable solution dosage form. As part of this study, the inventors discovered that the use of weak acid buffers was insufficient to bring about dissolution of TMP at a concentration great enough to achieve therapeutic dosage levels.

In the preferred method of preparing the composition, trimethoprim is mixed with purified water at 55° C., sufficient acid is added, and then the solution is mixed until completely dissolved. While cooling to room temperature, additional acid is added to adjust the pH to approximately 4.2. The preservative (e.g., methyl and propyl paraben dissolved in 3% propylene glycol) is added while mixing continues. The sweetener (e.g., sucrose dissolved in water) is added while mixing continues. The artificial sweetener (e.g., sodium saccharin) and the flavoring (e.g., bubble gum flavor) are added while mixing continues. The remaining purified water, possibly containing a suitable buffer mixture to ensure maintenance of the pH of the final mixture at 4.0 to 6.0, is added to bring the composition to its final volume.

EXAMPLES

Example 1

The following example describes the preparation of the TMP composition.

Procedure (per liter)
1. Heat 500 mL of water to 50°–55° C., and add 5.0 g of trimethoprim.
2. Without additional heating and while stirring, add hydrochloric acid to pH of 4.2–4.4, with pH meter temperature compensation, or 4.6 without meter compensation. This will require approximately 16 mL of 1N HCl per liter.
3. When the solution is clear, add methyl and propyl parabens dissolved in propylene glycol.
4. Add 450 mL simple syrup.
5. Cool to room temperature.
6. Add sodium saccharin and bubble gum flavor.
7. Bring to 1 liter volume with water.

The TMP composition gives the following characteristics:
Trimethoprim, Micronized, USP 5.000
Purified Water, USP approx 500
Hydrochloric Acid, 1N approx 16
Methyl Paraben, NF 0.500
Propyl Paraben, NF 0.050
Propylene Glycol, USP 30.000
Simple Syrup, USP 450.000
Saccharin Sodium, USP 1.500
N/A Bubble Gum Flavor, Crompton & Knowles #F1, W/S, All,236 2.000

Example 2

Physical Properties

A sample of the composition was subjected to freezing at a temperature of less than 0° C. for several days, allowed to thaw at room temperature, refrozen, rethawed, refrozen, and rethawed again. A visual examination of the sample revealed no crystallization of any substances from solution.

A sample of the composition was subjected to storage in a refrigerator at a temperature of less than 10° C. for several weeks. A visual examination of the sample revealed no crystallization of any substances from solution.

A sample of the composition was subjected to storage in an incubator at a temperature of 45° C. for several weeks. A visual examination of the sample revealed no discoloration or crystallization of any substances from solution.

Microbiological Properties

A sample of the composition was subjected to preservative effectiveness testing by a method similar to that described in volume 22 *United States Pharmacopeia*, "Antimicrobial Preservatives—Effectiveness," Test 51 (1990). The composition met the prescribed criteria at the 48 hour time period.

Chemical Stability Properties

A sample of the composition was subjected to storage at room temperature for several weeks. Chemical analysis of the sample revealed no degradation of trimethoprim and no physical evidence of deterioration with respect to color, flavor, or sweetness.

Although the foregoing invention has been described in some detail by way of illustration and example for purposes of clarity of understanding, it will be obvious to one skilled in the art that certain changes and modifications may be practiced within the scope of the appended claims.

What is claimed is:

1. A palatable pharmaceutical oral solution formulation for pediatric dosing consisting of:
    (a) about 1.25 to 8 mg trimethoprim per mL (wt./vol.) of purified water;
    (b) hydrochloric acid (HCl) in sufficient concentration with purified water to permit said trimethoprim to dissolve at the appropriate concentration, wherein the solution of dissolved trimethoprim has a pH of between 4.0 and 6.0; and
    (c) sucrose and flavoring, other than sucrose, in an amount sufficient to overcome the bitterness of said trimethoprim.

2. A palatable pharmaceutical oral solution formulation for pediatric dosing consisting of:
    (a) about 125 to 8 mg trimethoprim per mL (wt./vol.) of purified water;
    (b) sulfuric add ($H_2SO_4$) in sufficient concentration with purified water to permit said trimethoprim to dissolve at the appropriate concentration, wherein the solution of dissolved trimethoprim has a pH of between 4.0 and 6.0; and
    (c) sucrose and flavoring, other than sucrose, in an amount sufficient to overcome the bitterness of said trimethoprim.

3. The pharmaceutical oral solution formulation of any of claims 1 or 2 wherein said trimethoprim concentration is 5 mg/mL.

* * * * *